(12) United States Patent
Opperman et al.

(10) Patent No.: US 9,229,005 B2
(45) Date of Patent: *Jan. 5, 2016

(54) COMPOSITIONS AND METHODS FOR IN VITRO DIAGNOSTIC TESTS INCLUDING SULFONIC ACID COMPOUND

(71) Applicant: SurModics, Inc., Eden Prairie, MN (US)

(72) Inventors: Gary Opperman, St. Louis Park, MN (US); Wendy Nelson, Woodbury, MN (US)

(73) Assignee: SURMODICS IVD, INC., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/849,056

(22) Filed: Mar. 22, 2013

(65) Prior Publication Data
US 2013/0252261 A1 Sep. 26, 2013

Related U.S. Application Data

(60) Provisional application No. 61/614,602, filed on Mar. 23, 2012.

(51) Int. Cl.
| | |
|---|---|
| G01N 21/78 | (2006.01) |
| C12Q 1/28 | (2006.01) |
| G01N 33/58 | (2006.01) |
| G01N 33/52 | (2006.01) |
| G01N 33/535 | (2006.01) |
| G01N 33/558 | (2006.01) |

(52) U.S. Cl.
CPC .............. *G01N 33/581* (2013.01); *C12Q 1/28* (2013.01); *G01N 21/78* (2013.01); *G01N 33/52* (2013.01); *G01N 33/535* (2013.01); *G01N 33/558* (2013.01)

(58) Field of Classification Search
None
See application file for complete search history.

(56) References Cited

U.S. PATENT DOCUMENTS

| RE29,498 E | 12/1977 | Meiattini |
|---|---|---|
| 4,778,757 A | 10/1988 | Teshima et al. |
| 5,206,006 A | 4/1993 | Frontini et al. |
| 6,376,252 B1 | 4/2002 | Van Lente et al. |
| 6,517,778 B1 | 2/2003 | Kumar et al. |
| 7,727,739 B2 | 6/2010 | Whateley |
| 2004/0219620 A1 | 11/2004 | Mayer |
| 2005/0158815 A1 | 7/2005 | Akhavan-Tafti et al. |
| 2012/0009603 A1* | 1/2012 | Della Ciana et al. ........ 435/7.92 |
| 2014/0234874 A1* | 8/2014 | Opperman et al. ......... 435/7.92 |

FOREIGN PATENT DOCUMENTS

EP 2405016 A1 1/2012

OTHER PUBLICATIONS

Fossati et al., "Use of 3,5-dichloro-2-hydroxybenzenesulfonic acid/4-aminophenazone chromogenic system in direct enzymic assay of uric acid in serum and urine," Clin Chem., 1980, vol. 26, No. 2, pp. 227-231.*

Vojinović et al., "Assay of H2O2 by HRP catalysed co-oxidation of phenol-4-sulphonic acid and 4-aminoantipyrine: characterisation and optimization," J. Mol. Catal. B:Enzym., 2004, vol. 28, No. 2, pp. 129-135.*

A print-out retrieved Jul. 11, 2014 from http://en.wikipedia.org/wiki/Methanesulfonic_acid.*

A print-out retrieved Mar. 11, 2015 from https://fscimage.fishersci.com/msds/95551.htm.*

PCT Search Report for International Application No. PCT/US2013/033429 mailed on Jun. 19, 2013.

Andrews, P.C., and Krinsky, N.I. (1982) *Quantitative determination of myeloperoxidase using tetramethylbenzidine as substrate.* Anal Biochem. 127:346-350.

Bos, E.S., et al. (1981) *3,3',5,5'-Tetramethylbenzidine as an Ames test negative chromogen for horse-radish peroxidase in enzyme-immunoassay.* J. Immunoassay. 2:187-204.

Frey, A., et al. (2000) *A stable and highly sensitive 3,3',5,5"-tetramethylbenzidine-based substrate reagent for enzyme-linked immunosorbent assays.* J. Immunol. Methods 233:47-56.

Holland, V.R., et al. (1974) *A safer substitute for benzidine in the detection of blood.* Tetrahedron 30:3299-3302.

Josephy, P.D., et al. (1982) *The horseradish peroxidase-catalyzed oxidation of 3,3,3',5'-tetramethylbenzidine.* J. Biol. Chem. 257:3669-3675.

Josephy, P.D., et al. (1983) *Co-oxidation of benzidine by prostaglandin synthase and comparison with the action of horseradish peroxidase.* J. Biol. Chem. 258:5561-5569.

Keener, W.K., and Watwood, M.E. (2004) *Chloride analysis using 3,3',5,5'-tetramethylbenzidine and chloroperoxidase.* Anal. Biochem. 334:406-408.

Liem, H.H., et al. (1979) *Quantitative determination of hemoglobin and cytochemical staining for peroxidase using 3,3',5,5'-tetramethylbenzidine dihydrochloride, a safe substitute for benzidine.* Anal. Biochem. 98:388-393.

Morrell, J.I., et al. (1981) *Comparison of horseradish peroxidase visualization methods: quantitative results and further technical specifics.* J. Histochem. Cytochem. 29:903-916.

Ping, Z., et al. (2000) *Enzyme immunoassay using a crossed-beam thermal lens technique.* Microchemical Journal 64:257-262.

(Continued)

*Primary Examiner* — Galina Yakovleva
(74) *Attorney, Agent, or Firm* — Kagan Binder, PLLC (57) ABSTRACT

The invention provides compositions, kits, and methods for performing colorimetric analysis. A substrate is reacted to generate a chromogenic reaction product, and a reaction stop reagent that is a sulfonic acid is added to stop and stabilize the reaction product. The absorbance properties of the chromogenic reaction product can be maintained over significantly longer periods of time of that of conventional reagents and methods. The sulfonic acid can be used in assays such as ELISAs in order to provide a more accurate and safer detection of analytes in a biological sample.

7 Claims, 5 Drawing Sheets

(56) References Cited

OTHER PUBLICATIONS

Pinkus, J.L., and Goldman, L.S. (1977) *A Benzidine Rearrangement and the Detection of Trace Quantities of Blood.* Journal of Chemical Education 54:380-381.

Volpe, G., et al. (1998) *3,3',5,5'-Tetramethylbenzidine as electrochemical substrate for horseradish peroxidase based enzyme immunoassays. A comparative study.* Analyst, Jun. 123:1303-1307.

\* cited by examiner

COMPOSITIONS AND METHODS FOR IN VITRO DIAGNOSTIC TESTS INCLUDING SULFONIC ACID COMPOUND

CROSS-REFERENCE TO RELATED APPLICATION

The present non-provisional Application claims the benefit of commonly owned provisional Application having Ser. No. 61/614,602, filed on Mar. 23, 2012, entitled COMPOSITIONS AND METHODS FOR IN VITRO DIAGNOSTIC TESTS INCLUDING SULFONIC ACID COMPOUND, which Application is incorporated herein by reference in its entirety.

FIELD

The invention relates to compositions and methods for in vitro diagnostic tests and in vitro colorimetric tests.

BACKGROUND

Research and diagnostic procedures require rapid, accurate and qualitative and/or quantitative determinations of substances ("analytes") that are present in biological samples, such as biological tissues or fluids, at low concentrations. For example, the presence of drugs, narcotics, hormones, steroids, polypeptides, prostaglandins or infectious organisms in blood, urine, saliva, dental plaque, gingival crevicular fluid, and other biological specimens is desirably determined in an accurate and rapid fashion for suitable diagnosis or treatment.

In many cases, an analyte is identified in a sample using a compound that specifically recognizes the chemical features of the analyte. Often, monoclonal antibodies specific for one or more chemical epitopes on an analyte are used. The complex formed between the antibody and analyte can be detected by a variety of known methods. The most commonly used methods employ a signal generating moiety of some type which is either already attached to the antibody, or becomes attached to the antibody through further reaction. For example, in the formation of a complex of biotin with avidin, the complex may be detected using a label on either the avidin or biotin molecule. Such a label can be a radioisotope or an enzyme conjugated with the avidin or biotin. Alternatively, the avidin-biotin complex might be detected by further reaction with a labeled molecule which is specific to either or both parts of the complex. It is commonly known to do the same with antigens and their corresponding antibodies.

In diagnostic tests designed to be rapid and easy to use with moderate training in a doctor's office or clinic, the specific binding ligand of interest (such as an antigen from an infectious agent) is often detected using colorimetric, fluorescent or chemiluminescent signals resulting from reaction of the enzyme label with its corresponding substrate.

There is a need to produce the signal quickly and intensely if the ligand is present. This is commonly done using a colorimetric detection reagent. Upon addition of the detection reagent a colored product is produced. In many types of assay, the generation of color is not limited. In order to optimally quantitate the result, a stop reagent is employed to stop the formation of color and hold it at a stable level to allow for accurate quantitation. Acids such as sulfuric acid and hydrochloric acid can be used to stop the production of detectable signal when peroxidase is used as a label in specific binding reactions. However, the use of these acids has problems associated with it, namely corrosivity, short signal duration, and toxicity.

The investigator has discovered there is a need to provide a non-corrosive stop reagent and a stop reagent that allows for an extended dynamic range and a longer, more stable signal time than previous acids have provided.

SUMMARY

Generally, the invention provides compositions, kits, and methods for determination of an analyte in a sample which uses a chromogenic substrate detectable by colorimetric analysis, and a stop reagent for stopping and stabilizing a reaction composition comprising a chromogenic reaction product. The stop reagent is a sulfonic acid.

Experimental studies associated with the invention have unexpectedly found that the sulfonic acid stop reagents stabilize absorbance properties of the chromogenic reaction product over significantly longer periods of times as compared to assays using conventional stop reagents. In addition, the stop reagents of the invention allowed for colorimetric analysis, especially at high analyte levels, to be performed over an extended dynamic range. Advantageously, the stop reagents of the invention do not have the corrosivity characteristics of sulfuric and hydrochloric acids, which make the components and compositions of the kits and methods of the invention more amenable to handling.

Accordingly, one aspect of the invention provides a kit with components for performing a colorimetric assay. The kit comprises a chromogenic substrate capable of forming a chromogenic reaction product detectable using colorimetric analysis, and a compound that stops and stabilizes the chromogenic reaction product, the compound being a sulfonic acid. The kit can optionally include other components like one or more redox compounds, such as peroxidases, peroxidase substrates, oxidases and oxidase substrates, which can be used to convert the chromogenic substrate into the chromogenic reaction product. Another optional component is an analyte binding member, such as an antibody, capable of specific recognition of an analyte in a biological sample. Other optional components in the kit include vessels, such as multiwell plates, in which the colorimetric analysis can be carried out and the chromogenic reaction product read using spectrophotometric equipment.

The invention also provides a composition comprising the sulfonic acid and chromogenic reaction product detectable using colorimetric analysis. The chromogenic reaction product can be stabilized in the presence of the sulfonic acid. The composition can optionally include other components that can be used to generate the chromogenic reaction product such as a peroxidase, peroxidase substrate, oxidase, and oxidase substrate.

The method further provides methods for performing a colorimetric analysis. The method includes, in the least, a step of adding the sulfonic acid to a composition containing the chromogenic reaction product. The addition of the sulfonic acid stabilizes the chromogenic reaction product which can then be colorimetrically analyzed using equipment such as a spectrophotometer, or alternatively by visualization. The method can optionally include one or more steps upstream of the step of adding the compound with the sulfonic acid group. For example, the method can optionally include step(s) of providing a biological sample having an analyte, contacting the analyte with an analyte-binding compound, recognizing the analyte/analyte-binding compound complex with one or more components, such as a peroxidase, peroxidase substrate, oxidase, and oxidase substrate that promote conversion of a substrate, and formation of the reaction product detectable using colorimetric analysis.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The present invention is directed to compositions, kits, and methods for performing a colorimetric assay using sulfonic acid. Sulfonic acid is a compound that includes one or more sulfonic acid group(s) (—$SO_3H$). Sulfuric acid ($H_2SO_4$) is not a sulfonic acid. In experiments associated with the invention, it has been found that use of the sulfonic acid stop reagent provides distinct benefits in assays in which a chromogenic reaction product is detected by colorimetric analysis. The sulfonic acid stop reagent of the invention have been shown to stabilize the chromogenic reaction product so the loss of signal intensity or absorbance of the reaction product after the stop reagent is added is minimized. For example, after a color- or signal-generating reaction is carried out, the stop reagent is added to the reaction composition to maintain favorable color characteristics (e.g., as measured by optical absorbance) or signal intensity over extended periods of time. By comparison, more rapid changes in color characteristics (e.g., as measured by optical absorbance) are observed when known stop reagents such as sulfuric acid (as the only stop reagent in the composition) are used.

Minimizing loss of signal intensity or absorbance can provide a more accurate assessment of the amount of analyte in the sample. It can also afford the user with greater flexibility for carrying out colorimetric analysis, and therefore the user can optionally make the analysis process more complex, can optionally increase the throughput of the analysis (e.g., analyze more samples), or both. The decrease in signal intensity using known stop reagents such as sulfuric acid is particularly dramatic when the sample includes a high amount of analyte. In further experimental studies associated with the invention, it was shown that use of the sulfonic acid stop reagents of the invention greatly minimize the loss of signal intensity at high analyte levels. Accordingly, this improves the dynamic range of detection when stop reagents of the invention are used in a colorimetric analysis.

Exemplary sulfonic acid stop reagents comprise one ore more sulfonic acid groups (—$SO_3H$), but do not include sulfuric acid ($H_2SO_4$). Compounds that can be used as sulfonic acid stop reagents, including those described herein, are commercially available or can be prepared according to methods known in the art of chemical synthesis. Exemplary sulfonic acid stop reagents can include non-polymeric and polymeric compounds.

In some embodiments, the kits, composition, and methods use a sulfonic acid stop reagent of Formula I: R—$SO_3H$, wherein R is selected from the group consisting of alkyl, aminoalkylene, aminoalkyl, hydroxyalkyl, aryl, amine, fluoroalkyl, perfluoroalkyl, and wherein $R^1$ is a branched or straight chain alkylene group.

Exemplary alkylsulfonic acids include those where R is methyl, ethyl, or propyl, which provides methanesufonic acid (methylsulfonic acid; $CH_3SO_3H$), ethanesufonic acid (ethylsulfonic acid; $CH_3CH_2SO_3H$), and propanesufonic acid (propylsulfonic acid; $CH_3CH_2CH_2SO_3H$), respectively.

In some cases the sulfonic acid includes an amine group. For example, if R is —$NH_2$ then the compound is sulfamic acid (also known as amidosulfonic acid, amidosulfuric acid, aminosulfonic acid, and sulfamidic acid; $H_2NSO_3H$). Other amine-group-containing sulfonic acids are aminoalkylenesulfonic acids, such as aminomethanesulfonic acid, 2-aminoethanesulfonic acid (taurine), and aminoproanesulfonic acid.

In some cases the sulfonic acid is an arylsulfonic acid, such as p-toluenesulfonic acid (PTSA; tosylic acid), xylenesulfonic acid, and cumenesulfonic acid.

In more specific embodiments, when R is compounds of Formula II are provided:

with exemplary $R^1$ groups including methylene (—$(CH_2)$—), ethylene (—$(CH_2CH_2)$—), methylmethylene dimethylmethylene methylethylene and dimethylethylene where Formula II includes compounds such as 2-acrylamido-2-methylpropane sulfonic acid, 2-acrylamido propane sulfonic acid, and 2-acrylamido ethane sulfonic acid.

The invention also contemplates stop reagents having two or more sulfonic acid groups, such as disulfonic acids. Commercially available disulphonic acids include, for example, 2-naphthol-3,6-disulfonic acid, phenol disulfonic acid, ethanedisulfonic acid, and aniline disulfonic acid. Polymers containing two or more sulfonic acid groups, exemplified by those derived from acrylamide described, above, are also contemplated.

Optionally, the stop reagent of the invention can be referred to as a "sulfonic acid derivative" which refers to compounds represented by sulfonic acid compounds and formulas such as those described herein which is not sulfuric acid.

In some embodiments, structures of exemplary sulfonic acids are represented in Table 1 below.

TABLE 1

| Designation | Structure |
|---|---|
| dodecylbenzenesulfonic acid (DBSA) | |
| 4,5-dihydroxy-1,3-benzenedisulfonic acid | |
| 3-hydroxypropane-1-sulfonic acid | |
| 4,4'-diamino-2,2'-stilbenedisulfonic acid | |
| methanesulfonic acid | |
| ethanesulfonic acid | |
| propanesulfonic acid | |

TABLE 1-continued

| Designation | Structure |
|---|---|
| (4-(2-hydroxyethyl)-1-piperazineethane-sulfonic acid ) (HEPES) | *[structure]* |
| 3-(N-morpholino)propane-sulfonic acid (MOPS) | *[structure]* |
| 3-(N-morpholino)-2-hydroxy-1-propanesulfonic acid (MOPSO) | *[structure]* |
| perfluorooctanesulfonic acid | *[structure]* |
| triflic acid | *[structure]* |
| p-toluenesulfonic acid (PTSA) | *[structure]* |
| sulfamic acid | *[structure]* |

TABLE 1-continued

| Designation | Structure |
|---|---|
| taurine | *[structure]* |

The sulfonic acid can also be described in terms of its acid dissociation constant ($pK_a$; or acid ionization constant). Sulfonic acid stop compounds of the invention may have more than one acid dissociation constant depending on the protonic or zwitterionic nature of the compound. For purposes of discussion, if the compound has more than one acidic dissociation constant, the compound's $pK_a$ refers to its lowest (most acidic) acid dissociation constant. In some cases the sulfonic acid stop compound has a $pK_a$ in the range of about 4 to −3, or in the range of about 4 to about −2.5, or in the range of about 4 to about −2, or in the range of about 3 to about −2.5, or in the range of about 2 to about −2.5, or even in the range of about 1 to about −2.5.

The sulfonic acid stop compound can also be described in terms of its liquid solubility. Since colorimetric assays are commonly performed in a water-based solution, such as a buffered aqueous solution, in many embodiments the sulfonic acid stop compound is at least slightly soluble in water. Descriptive terms for solubility are standard terms used in the art (see, for example, *Remington: The Science and Practice of Pharmacy*, 20th ed. (2000), Lippincott Williams & Wilkins, Baltimore Md.), with "slightly soluble" referring to compounds having a solubility of 1 part agent per from 100 to 1000 parts of solvent; "sparingly soluble" referring to compounds having a solubility of 1 part agent from 30 to 100 parts of solvent; "soluble" referring to compounds having a solubility of at least 1 part compound per from 10 to 30 parts solvent, "freely soluble" refers to compounds having a solubility of at least 1 part agent per from 1 to 10 parts solvent, and "very soluble" refers to having a solubility of greater than 1 part agent per from 1 part solvent.

Compositions of the invention based on aqueous solutions can optionally be formulated to include water soluble co-solvents or components that can improve the solubility of components in the composition (e.g., the stop reagent) if desired. Examples of useful optional co-solvents are alcohols (i.e. methanol, ethanol, propanol), polyalcohols (i.e. glycerol, propylene glycol), dimethylsulfoxide, dimethylformamide, acetonitrile, and similar solvents. Other solvents to improve solubility are well known in formulation art for in vitro diagnostic applications, can optionally be included in compositions of the invention. Other solubility-enhancing components such as described in U.S. Provisional No. 61/751,652 (Jan. 11, 2013; Lundquist) can be included in the composition and/or kit of the invention.

In some cases, a sulfonic acid stop reagent of the invention can be mixed with one or more other sulfonic acid stop reagent(s) of the invention. For example, kits, compositions, and methods of the invention can include a mixture of methanesulfonic acid and sulfamic acid. Optionally, a stop reagent of the invention can be mixed with one or more other stop reagent(s) already known in the art of colorimetric assays.

Sulfonic acid stop reagents of the invention can be provided in solid or liquid form, depending on the properties of the compound, and the desired arrangement of the kit or composition. If the sulfonic acid stop reagent is a liquid at ambient conditions, it can be supplied and/or used in neat form, or can be diluted with a suitable solvent, such as water.

In some embodiments the sulfonic acid stop reagent can be supplied in a dry form (e.g., powder, granule, pellet, etc.) and then be dissolved prior to use by using an appropriate solvent. In yet other embodiments the sulfonic acid stop reagent can be dissolved by mixing with a known liquid stop reagent (e.g. $H_2SO_4$).

The kits, compositions, and methods of the invention can also include a chromogenic substrate (or a reaction product of the substrate; "chromogenic reaction product") for colorimetric analysis. In an assay, the chromogenic substrate is subjected to a chemical reaction, such as one associated with an enzymatic reaction, resulting in a chromogenic "reaction product" detectable using colorimetric analysis. For example, in an assay, a chromogenic substrate can undergo chemical oxidation or reduction, or chemical modification by the addition, subtraction, or rearrangement of chemical groups on the chromogenic substrate. The reaction product can be one where, for example, the oxidized or reduced form the chromogenic substrate, or a chemically-modified form of the chromogenic substrate, is detectable by colorimetric analysis.

In some embodiments the chromogenic substrate can be a compound that is uncolored, or one that has a first color, or one that does not emit a signal, or combinations thereof. The chromogenic reaction product can be colored, have a (second) color that is different than the first color, or emit a signal, or combinations thereof. In some cases the chromogenic reaction product is formed by the reaction of two starting compounds which produces a chromogenic substrate that is oxidized to produce a colored chromogenic reaction product.

A variety of known chromogenic substrates for colorimetric analysis can be used in the kits, compositions, and methods of the invention. Chromogenic substrates contemplated for use with the current invention include benzidine, ortho-tolidine, ortho-dianisidine, which can change color in the presence of peroxidase-containing components. In some embodiments, the kits, compositions, and methods of the invention use a benzidine derivative such as 3,3',5,5'-tetramethylbenzidine. Benzidine derivatives include those of formula III:

where X, X', Y, Y', R, and R' are independently hydrogen, alkyl, alkoxy, or combinations thereof, wherein the alkyl or alkoxy group(s), if present, having up to six carbon atoms. In more specifically aspects of formula III, X, X', Y, Y', R, and R' are independently hydrogen, alkyl, alkoxy, or combinations thereof, wherein the alkyl or alkoxy group(s), if present, containing four or less carbon atoms. Benzidine-type compounds include 3,3',5,5'-tetramethylbenzidine, o-tolidine, o-dianisidine, N,N,N',N'-tetramethylbenzidine. See, for example, U.S. Pat. No. 6,376,252.

In the presence of horseradish peroxidase (HRP) and hydrogen peroxide tetramethylbenzidine (3,3',5,5'-tetramethylbenzidine; TMB) is oxidized to form colored products. As described by Josephy et al. (1982; J. Biol. Chem. 257: 3669-3675), TMB ($\lambda_{max}$ 285) is oxidized to form oxidized TMB, a blue product ($\lambda_{max}$ 652) which is a one-electron oxidation product, and then is further oxidized to form a yellow product ($\lambda_{max}$ 450), which is the two-electron oxidation product. Colorimetric analysis and measurement of the reaction product is typically carried out at 450 nm, but can also be observed with the unaided human eye (Reaction Sequence A).

$\lambda_{max} = 450$ nm

Other chromogenic material includes Trinder reagents which use a phenylpyrazone derivative and a phenolic or an aromatic amine compound. In the chemistry of peroxidase reactions with Trinder reagents, two colorless organic molecules form a colored product in the presence of peroxidase and hydrogen peroxide. Exemplary phenylpyrazone derivatives include 4-aminoantipyrine, and exemplary phenols include cresol and salicylamide; other exemplary phenylpyrazone derivatives and phenols are described in U.S. Pat. No. RE29,498. Exemplary aromatic amines include N,N-dialkylaniline compounds, N,N-dialkyl-m-toluidine compounds, toluidine and aniline sulphopropyl derivatives, N-ethyl-N-(3-sulphopropyl)-m-anisidine and N-ethyl-N-(2-hydroxyethyl)-m-toluidine, as described in U.S. Pat. No. 5,206,006.

Other chromogenic material includes OPD (o-phenylenediamine) which is a water-soluble substrate for horseradish peroxidase (HRP) that produces a yellow-product detectable at 450 nm. Addition of acid to the OPD reaction product produces a yellow-orange with an absorbance maximum of 492.

Tyramine is used as a substrate in dopamine-beta-hydroxylase (DBH) assays. DBH converts 3,4-dihydroxyphenylethylamine(dopamine) into the neurotransmitter norepinephrine. Tyramine is converted by DBH to octopamine, which is then oxidized to parahydroxybenzaldehyde by sodium periodate. The oxidation is stopped by sodium metabisulfite. Parahydroxybenzaldehyde is then quantified by measuring its absorbance at 330 nm.

The water-soluble HRP substrate 2,2'-azino-di(3-ethylbenzthiazoline-6-sulfonate) (ABTS) yields a green end product upon reaction with peroxidase. The green product has two major absorbance peaks, 410 nm and 650 nm. ABTS is less sensitive than OPD and TMB in ELISA applications. It is less readily oxidized, and its color development is slower (approximately 20-60 minutes).

Other chromogenic material that can be used in the methods, kits, and compositions of the invention includes the tetrazolium dye, MTT, which can be reduced to insoluble formazan, which is purple.

Aspects of some embodiments of the present disclosure relate to the use of the sulfonic acid stop reagent comprising with colorimetric assays. Generally, colorimetric analysis can be performed to determine the presence and/or amount of an analyte in a sample. The term "analyte" refers to any substance or chemical constituent of a sample that is being analyzed. The analyte can be a natural compound, such as one that is produced by an organism, or can be a non-natural compound, such as a synthetic compound used as a bioaffecting agent like a drug, a pesticide, or herbicide. Methods, compositions, and kits of the invention can be used for the determination of analytes in numerous industrial applications including, but not limited to health care, food manufacture and processing, chemical analysis and production, agriculture, environmental control, and the like. In some aspects, an ELISA (enzyme-linked immunosorbent assay) is used for detection of an analyte, and the ELISA and/or or kit used to perform an ELISA incorporates the sulfonic acid stop reagent of the invention.

As described herein, in some modes of practice, a colorimetric analysis or colorimetric assay can be conducted using specialized equipment known in the art to quantify and measure the wavelength and/or absorbance of the solution being analyzed. Such equipment includes, but is not limited to UV-visible spectrophotometers and multiwell plate readers. In some embodiments, the colorimetric analysis or colorimetric assay may be conducted, and endpoint determined, using the unaided human eye.

Various types of analytes can be detected and quantified in a sample using the methods of the invention. In some aspects, detection of the analyte is facilitated by using an analyte binding member, such as an antibody. In other aspects, methods of the invention provide for detection of an analyte without utilizing an analyte binding member. Non-limiting exemplary analytes include drugs, drug metabolites, biomarkers, hormones, antibiotics, food supplements, food additives, naturally occurring contaminants, dyes, microorganisms and their toxins, fungi, viruses, pesticides, herbicides, organic components of waste discharges, tissue specific markers, tissue specific enzymes, cytokines, chemokines, growth factors, receptor ligands, enzymes, nucleic acids, lipids, and small organic molecules, such as glucose and peroxides.

For example, in the food processing and manufacturing industries for humans, as well as domesticated and farm animals, ELISAs are used for the detection of various analytes that are polypeptides, such as soy proteins and gluten, which can be allergens, and other compounds such as antibiotics and hormones.

As other non-limiting examples, in the health care industry ELISAs are used for the detection of various analytes in blood, urine, and other body fluids for the detection of analytes such as erythropoietin (EPO), adrenocorticotropic hormone (ACTH), calcitonin, parathyroid hormone (PTH), thyroid stimulating hormone (TSH), prostate-specific antigen (PSA), human chorionic gonadotropin (HCG), follicle stimulating hormone (FSH), growth hormone (GH).

In some embodiments, the kit, composition, or method of the invention is configured for detection of a nucleic acid analyte. Any type of nucleic acid capable of interacting with a complimentary nucleic acid sequence can be detected as the analyte. Exemplary analytes include nucleic acid fragments (e.g., restriction digested DNA) of bacterial, viral, and eukaryotic DNA, including genomic DNA, plastid DNA, mitochondrial DNA, etc.; as well as mRNA (messenger RNA), iRNA (immune ribonucleic acid), ribozymes, siRNA (small interfering RNA), miRNA (micro RNA), and shRNA (short hairpin RNA).

The sample including an analyte to be detected can be a biological or a non-biological sample.

A biological sample can be any material taken from an organism such as body fluid from a mammal, material derived from an organism, or a sample that has organisms in it. Biological samples include certain tissues, or body fluid such as blood, sputum, urine, saliva, mucus, vitreal fluid, synovial fluid, semen, cerebrospinal fluid, bone marrow, amniotic fluid, bile, sweat, etc. Biological samples can be obtained from patients and analyzed for the absence or presence of analytes associated with disease states. Quantitation of an analyte can be used to determine the absence, presence or degree of a disease state. Biological samples can also include sections of tissues such as frozen sections taken for histological purposes which can also be analyzed for analytes associated with disease states.

Other samples, including biological samples, can be those derived from fermentation, cell culturing, bio-fuel production, wastewater treatment, and agriculture. These include food products such as milk, wine, beer, and the like; chemical streams, or waste streams from chemical plants, rivers, and the like. If the sample is initially complex, solid, or viscous, it can optionally be treated, such as by extraction, or it cam be dissolved or diluted in order to obtain a sample having the appropriate characteristics for use in the immunoassay.

An example of a non-biological sample is a composition of a chemically-synthesized component, such as a synthetic drug for human treatment or a synthetic pesticide for agricultural use.

Analyte detection and the chromogenic assay can be performed in a suitable assay vessel. An assay vessel is any suitable receptacle in which analyte detection, such as by ELISA, and the chromogenic assay can be performed. The assay vessel can be made from material such as glass (e.g., surface modified glass), quartz, or plastic, such as polystyrene, polypropylene, and polycarbonate. Exemplary assay vessels are single and multi-well plates, such as medium and smaller-welled plastic plates such as 6, 24, 96, 384, and 1536 well plates. These are commonly known in the art as microtiter plates, microplates, or microwell plates. Exemplary plates for use in chromogenic assays in each well can hold from microliter to milliliter volumes of liquid. Other types of assay vessels that can be used for analysis include capillary tubes. The assay vessel can optionally be included in a kit, or can be supplied by the user to carry out chromogenic assay methods as described herein.

For example, in some modes of practice, 96-well plates are used for analyte detection and the chromogenic assay. A single well in a 96-well plate generally holds up to about 300 μL to 350 μL of liquid, and all or a fraction of this volume can be used during steps in methods of the invention. This can provide a convenient volume for steps in ELISA chromogenic assays, involving antibody, analyte, and enzyme immobilizations, dispensing a biological sample, washing steps, dispensing a chromogenic substrate, and the addition of a stop reagent for the colorimetric analysis. The area on the bottom of a 360 μL well is about 0.32 cm$^2$.

In some cases, it is not necessary to identify the analyte (to be detected) in the biological sample with an analyte binding member, such as an antibody. Some assays use enzymes to measure certain biological substances in samples. For example, some assays use a peroxidase enzyme to measure peroxides present in a sample. Conversely, some assays detect the presence of biological enzymes by using the enzyme's corresponding substrate. For example, addition of hydrogen peroxide to a sample can be used to test for peroxidase enzymatic activity in the sample.

In some aspects of the invention, the sulfonic acid stop reagent is used in an enzyme-linked immunosorbent assay (ELISA). Generally, an ELISA uses a solid-phase immunoassay to detect the presence of an analyte in a liquid sample. Various ELISA formats are known in the art and any of these can be used in conjunction with the sulfonic acid stop reagent of the invention. Although antibodies are typically used in ELISAs, any sort of analyte-binding member can replace the antibody to provide analyte-specific interaction. As such, kits, composition, and methods of the invention can be used with any enzyme-linked solid phase analyte binding assay. The methods of the invention can include any analyte-binding reagent immobilized on the solid phase, along with a chromogenic reagent that can be detected using colorimetric analysis in the presence of an enzyme. The invention is not limited to any type of analyte binding assay, or any type of analyte binding member, but some examples are discussed to illustrate aspects of the invention. The particular immunoassay format employed will depend on the particular analyte characteristics, the sample characteristics, the available reagents, and the like.

One example of a common ELISA format is the "direct, antigen down" ELISA which is often used when the biological substance measured is antibody. In this format a purified protein (the antigen) is absorbed to the plastic surface of a multi-well plate. The plate is washed to remove excess antigen and then blocked with a blocking agent that can be protein based or synthetic, to prevent non-specific binding of the antibody. Next, a sample is added to the well that includes antibodies that specifically bind the antigen immobilized on the plastic surface. Excess sample is then washed off. After washing, secondary antibody conjugated to a peroxidase enzyme specific for the animal antibody in the biological sample is added. For example, if the sample is human, an anti-human antibody (e.g., an anti-human IgG) is used for detection. A chromogenic reaction can then be performed by adding a chromogenic substrate and a reactant, such as hydrogen peroxide, for the peroxidase. A sulfonic acid stop reagent of the invention can then be added to the chromogenic reaction, and colorimetric analysis can be performed using a spectrophotometer.

In other cases, for example, a "sandwich" ELISA can be performed by first immobilizing the analyte binding member (e.g., an analyte "capture" antibody) on the solid substrate, such as a plastic well. The plastic surface is then typically blocked with a non-specific protein to prevent adherence of components from the biological sample when added to the well in a next step. Analyte from the biological sample added to the well specifically interacts with the immobilized antibody on the plate. The plate is washed and then a solution of a second analyte binding member (such as an antibody conjugated to a peroxidase enzyme, called a detection antibody) is added which interacts with the analyte already immobilized by the plastic bound antibody. The analyte therefore effectively becomes "sandwiched" between the antibody absorbed on the plate, and the enzyme-conjugated antibody. A chromogenic reaction can then be performed by adding a chromogenic substrate and a reactant, such as hydrogen peroxide, for the peroxidase. A sulfonic acid stop reagent of the invention can then be added to the chromogenic reaction, and colorimetric analysis can be performed using a spectrophotometer.

Alternatively, the "sandwich" approach can be performed by first mixing an enzyme-conjugated antibody with a biological sample having an analyte. The enzyme-conjugated antibody is used in excess and analyte-enzyme-conjugated antibody complex forms in the sample. The sample is then transferred to a well of an assay plate that has the analyte capture antibody immobilized thereon. The analyte capture antibody binds the analyte-enzyme-conjugated antibody complex, and then the well can be washed to remove non-bound material. A chromogenic reaction can then be performed and then a sulfonic acid stop reagent can be added, as described.

Kits of the invention can include one or more components, other than the sulfonic acid stop reagent and the chromogenic substrate, useful for performing an ELISA. The kit can include optional components such as analyte-binding members like antibodies, enzymes (e.g., HRP-linked anti-IgG antibodies, etc), and enzyme substrates. The kit can also include vessels, such as multi-welled plates, in which the chromogenic reaction can take place and be analyzed. The kit can also include a solubility-enhancing component.

As described herein and in some aspects, the assay uses a compound having specific affinity for the analyte. A compound with specific affinity is referred to herein as a "binding moiety," which refers to any sort of chemical group that can bind or interact with the analyte. The binding moiety can include naturally occurring molecules or derivatives of naturally occurring molecules, or synthetic molecules, such as small organic molecules, or larger synthetically prepared molecules, such as polymers. Examples of binding moieties include polypeptides, nucleic acids, polysaccharides, and portions of these types of molecules that can bind a target species. Nucleic acids such as oligonucleotides that have a length sufficient to undergo complimentary hybridization to a target nucleic acid analyte in a sample can be used as the analyte binding moiety.

The binding moiety can be an antibody, which is a protein that recognizes a particular epitope on the analyte. In this regard, the analyte can also be referred to as an "antigen" as it is common for antibody-antigen interactions to be described. An antibody can be a polyclonal antibody, a monoclonal antibody, or a genetically engineered molecule capable of binding the corresponding member of a specific binding pair. One class of polypeptides that can be used as a binding moiety in the invention includes antibodies and antibody fragments.

Antibody and antibody fragments having specificity towards desired analytes are commercially available or can be prepared by techniques known in the art. For example, monoclonal antibodies (mAbs) can be obtained by any technique that provides for the production of antibody molecules by continuous cell lines in culture. These include, for example, the hybridoma technique (Kohler and Milstein, Nature, 256: 495-497 (1975)); the human B-cell hybridoma technique (Kosbor et al., Immunology Today, 4:72 (1983); and the EBV-hybridoma technique (Cole et al., Monoclonal Antibodies and Cancer Therapy, Alan R. Liss, Inc., pp. 77-96 (1985)). Such antibodies can be of any immunoglobulin class including IgG, IgM, IgE, IgA, IgD and any subclass thereof.

Fab or Fab'2 fragments can be generated from monoclonal antibodies by standard techniques involving papain or pepsin digestion, respectively. Kits for the generation of Fab or Fab'2 fragments are commercially available from, for example, Pierce Chemical (Rockford, Ill.).

In some embodiments the analyte binding member comprises a nucleic acid. For example, a nucleic acid having a sequence capable of hybridizing with a nucleic acid analyte under stringent conditions can be immobilized on a plastic or glass surface and used in the kit or method of the invention. Nucleic acid from a sample, such as a biological sample, can be placed in contact with the surface with immobilized nucleic acid. Nucleic acid analyte can be present from a cell sample that is treated to disrupt the cells and optionally enrich the analyte nucleic acid. Analyte nucleic acid can undergo hybridization by complimentary bonding to the immobilized nucleic acid. Stringent hybridization conditions are well known in the art (see for example, in Sambrook et al., Molecular Cloning: A Laboratory Manual, Second Edition, Cold Spring Harbor Laboratory, Cold Spring Harbor, N.Y., (1989)). Presence of the analyte can then be detected with a free probe (non-immobilized) nucleic acid that can hybridize to the nucleic acid analyte and that is either directly attached to an enzyme, or that can be indirectly coupled to an enzyme.

In other modes of detection, a nucleic acid from a sample is immobilized on a glass or plastic substrate, and then presence of the analyte can be detected with a free probe (non-immobilized) nucleic acid that can hybridize to the nucleic acid analyte and that is either directly attached to an enzyme, or that can be indirectly coupled to an enzyme.

In some cases, the binding moiety is conjugated to another compound which facilitates the colorimetric analysis, such as described herein.

In some aspects of the invention, the methods, compositions, or kits of the invention include an oxidase or a peroxidase. As a general matter, an oxidase or a peroxidase can be used to generate a radical resulting in the transfer of electrons from one component to another. When the chromogenic substrate is present, it becomes oxidized to a chromogenic product which is used in conjunction with the sulfonic acid stop reagent of the invention.

In some cases the oxidase or peroxidase is coupled to a binding moiety for the detection of an analyte. In these cases, the oxidase or peroxidase can simply serve to cause reduction of a peroxide compound, such as hydrogen peroxide, providing a chemical environment for the oxidation of the chromogenic substrate to a desired colored reaction product. Commercially available peroxidase conjugates, such as those described herein, can be used.

In other cases the oxidase or peroxidase has specificity towards an analyte of interest in the biological sample. For example, glucose oxidase (GOx) (EC 1.1.3.4) is an oxidoreductase that catalyses the oxidation of glucose to hydrogen peroxide and D-glucono-δ-lactone. In order to quantitate the amount of glucose in a biological sample, glucose oxidase and a peroxidase, such as horseradish peroxidase, can be added directly to the sample. Glucose oxidase, which causes the formation of hydrogen peroxide, can be reduced to provide conditions resulting in the oxidation of the chromogenic substrate. Xanthine oxidase is another enzyme that generates hydrogen peroxide by using hypoxanthine and xanthine as substrates. L-gulonolactone oxidase (EC 1.1.3.8) catalyzes the reaction of D-glucuronolactone to L-xylo-hex-3-gulonolactone and hydrogen peroxide. Using this type of approach, the analyte or the analyte binding member does not have be immobilized on a solid surface, such as performed using ELISA. Other oxidases include galactose oxidase, hexose oxidase, and pyranose oxidase.

Peroxidase enzymes useful for the methods of the invention can be obtained from a variety of sources, such as plants. Common, commercially available peroxidases are from horseradish and soybean. Horseradish peroxidase has an approximate molecular weight of 44 kDa, and is a single chain polypeptide glycoprotein with disulfide bridges that includes hemin plus $Ca^{2+}$. HRP specific activity can be expressed in pyrogallol units (one pyrogallol unit will form 1.0 mg purpurogallin from pyrogallol in 20 sec at pH 6.0 at 20° C.) or ABTS units (one ABTS unit will oxidize 1 μmole of ABTS per minute at 25° C. at pH 5.0). HRP can be inhibited by sodium azide, L-cystine, dichromate, ethylenethiourea, hydroxylamine, sulfide, p-aminobenzoic acid, $Cd^{+2}$, $Co^{+2}$, $Cu^{+2}$, $Fe^{+3}$, $Mn^{+2}$, $Ni^{+2}$, and $Pb^{-2}$.

Other peroxidases include lactoperoxidase, microperoxidase, NADH peroxidase NADPH peroxidase, fatty-acid peroxidase, and catalase.

In some modes of practice, a "peroxidase conjugate" is used in the methods for detecting an analyte. A conjugate generally refers to a compound that comprises two substances, wherein one of the substances is coupled to the other. Coupling of the conjugate can be covalent or non-covalent. A peroxidase conjugate can be one where a peroxidase enzyme is coupled to a binding moiety that detects the analyte, or that detects the binding moiety that detects the analyte. Exemplary peroxidase conjugates that can be commercially obtained include avidin-peroxidase conjugates, monoclonal anti-FLAG™ M2-peroxidase conjugates, anti-glutathione-S-transferase (GST)-peroxidase conjugates, anti-mouse IgG-peroxidase conjugates, anti-goat/sheep IgG-peroxidase conjugates, Protein G-peroxidase conjugates, Protein-A peroxidase conjugates, anti-rabbit IgG-peroxidase conjugates, and strepavidin-peroxidase conjugates, from, for example, Sigma-Aldrich.

A biological sample that includes an analyte can be placed in an analysis vessel, such as a well in a multiwall plate, so the analyte can be immobilized and then detected using methods of the invention. Typically, steps for the immobilization of the analyte or analyte binding member (e.g., antibody), binding of analyte binding member to the analyte, and subsequent binding of the analyte-analyte binding member complex can be performed using a suitable solution(s), including incubation, blocking, and washing buffers. The solution can be an aqueous buffered solution, to maintain absorption of the analyte and/or analyte binding member on the plastic surface, and maintain protein configuration for proper binding and enzymatic activities. The blocking solution can include a non-specific protein such as bovine serum albumin, which can effectively block vessel binding sites that remain following initial coating steps in ELISA procedures (e.g. 5% BSA-PBS). Washing buffers can include a surfactant such as Tween (an exemplary washing buffer, PBS-T, contains 10 mM phosphate buffer pH 7.4, 150 mM NaCl, and 0.05% Tween 20).

In some modes of practice, an analysis vessel (such as a multi-well plate) is provided that has an amount of peroxidase immobilized on a solid surface of the vessel. Again, the peroxidase can be immobilized by its conjugation to a binding member, with the binding member directly or indirectly bound to an analyte previously immobilized on the vessel surface, using either an analyte binding member, or by the analyte being absorbed directly on the surface of the vessel. The amount of immobilized peroxidase can correlate with the amount of immobilized analyte, which correlates with the amount of analyte present in a sample. In control wells, standards with known amounts of analyte can be used.

In order to explain modes of practicing of the invention, in exemplary embodiments, analyte immobilization results in the corresponding immobilization of picogram quantities of a peroxidase enzyme, such as horseradish peroxidase, on a surface of a single well of a 96-well plate, such as an amount in the range of about 0.1 pg to about 100 ng (100000 pg), about 1 pg to about 10 ng (10000 pg), or about 1 pg to about 1 ng (1000 pg). In this case, the peroxidase enzyme is immobilized prior to adding the enzyme substrate and chromogenic reagent.

As a general matter, a peroxide substrate is added to the peroxidase, which is immobilized on a surface of the vessel, or present in solution in the vessel. A cost-effective substrate for carrying out peroxidase reactions is hydrogen peroxide. HRP combines with hydrogen peroxide ($H_2O_2$) and can carry out heterolytic cleavage of the $H_2O_2$ oxygen-oxygen bond. The complex can oxidize a wide variety of chromogenic substrates, and then the reaction can be stopped by the addition of a sulfonic acid stop reagent such as one described herein.

Hydrogen peroxide and the chromogenic substrate can be present in a reaction solution, which can be added to a reaction vessel that includes the peroxidase enzyme. The reaction solution can be prepared from components of a kit that include the chromogenic substrate, hydrogen peroxide, reaction buffer. In some embodiments the hydrogen peroxide and chromogenic substrate are supplied in a ready-to-use one component composition or solution. In other embodiments the chromogenic substrate and hydrogen peroxide are provided to a user separately, in a kit. For example, hydrogen peroxide can be provided as a concentrated stock solution (e.g., ~2-3%). The concentrated hydrogen peroxide can be diluted in the reaction solution to exemplary amounts in the range of about 0.1 mM to about 50 mM (~3×10$^{-4}$% to ~0.17%), or about 0.5 mM to about 10 mM (~0.0017% to ~0.034%). The kit can also include a reaction buffer, such as sodium phosphate (pH 7-8) provided in dry or concentrated form. For example, the buffer can be supplied as a 5× or 10× concentrate which can then be diluted in the reaction composition to a working concentration, such as in the range of about 10 mM to about 75 mM.

The chromogenic substrate can optionally be reconstituted from dry form or diluted from a stock solution and then added to the reaction solution. Depending on the type of chromogenic substrate, the kit can optionally include one or more different liquids, such as dimethylsulfoxide (DMSO), if dissolution of the chromogenic substrate would be facilitated using such components. The working concentration of the chromogenic substrate can be chosen based on factors such as the type of chromogenic substrate, the amount of hydrogen peroxide, and/or the amount of analyte (and corresponding peroxidase) in the sample being analyzed. Exemplary ranges of the chromogenic substrate are from about 0.5 µM to about 10 mM, from about 10 µM to about 5 mM, or about 100 µM to about 3 mM.

Optionally, a cosolvent can be included in the reaction composition with the analyte, enzyme, and chromogenic substrate. The cosolvent can ensure the reagents of the reaction composition be maintained in soluble form and do not precipitate out of solution during the reaction, or later, such as upon addition of the stop reagent. Exemplary co-solvents include alcohols (i.e. methanol, ethanol, propanol), polyalcohols (i.e. glycerol, propylene glycol), dimethylsulfoxide, dimethylformamide, acetonitrile and similar solvents. Other solvents to improve solubility are well known in formulation art for in vitro diagnostic applications, and are included herein. A cosolvent can be used in the reaction composition, at exemplary concentrations in the range of about 1% (v/v) to about 50% (v/v), or about 5% (v/v) to about 25% (v/v).

A solubility-enhancing components such as described in U.S. Provisional No. 61/751,652 (Jan. 11, 2013; Lundquist) can optionally be included in the reaction composition.

In some modes of practice, the reaction solution that includes the components sufficient for color development of the chromogenic substrate can then be added directly to the vessel that includes the peroxidase enzyme. Alternatively, components of the kit can be mixed directly in the wells. Using multiwall plates, the reaction solution can be dispensed, for example, by pipetting, in the well manually or using automated apparatus. Multi-tip pipetting apparatus can be used to increase the speed of the dispensing and or mixing process. Using a 96-well plate format, typical reaction volumes range from about 25 μL to about 200 μL, or from about 50 μL to about 150 μL.

The peroxidase reaction resulting in the conversion of the chromogenic substrate into the chromogenic product can be carried out for a desired period of time at a desired temperature. The reaction can be monitored visually or spectrophotometrically to determine the development of color in the composition. The incubation step will typically occur at room temperature, although a temperature in the range of about 10° C. to about 50° C. can be employed. Incubation times will typically range from about 1 to about 60 minutes, or more usually about 5 to about 45 minutes.

In order to describe aspects of the invention, 3,3',5,5'-tetramethylbenzidine (TMB) is used as the chromogenic substrate in the presence of an immobilized HRP enzyme (associated with the analyte) and hydrogen peroxide. TMB, in the presence of HRP and $H_2O_2$ is oxidized to form a blue product ($\lambda_{max}$ 652), as previously described. The reaction can be observed visually, or the absorbance of the reaction can be monitored spectrophotometrically (e.g., at about 650 nm) to obtain an absorbance value corresponding to the blue color. The stop reagent can be added when the reaction reaches a desired color, or when a certain absorbance value is reached. For example, in the case of TMB oxidation, or other chromogenic substrates that have similar absorbance properties upon oxidation, the stop reagent can be added to the reaction composition when the wells with the highest signals reach an absorbance of up to about 1.6 absorbance units at about 650 nm. Addition of the stop reagent converts the blue reaction product to a yellow product with an absorbance maxima at about 450 nm. The extinction coefficient of the yellow TMB product is about 2.3 times that of the blue TMB. Allowing the blue product to develop to about 1.5 or 1.6 absorbance at 650 nm results in an absorbance between 3.5 and 4 absorbance units upon the addition of stop reagent, which represents a practical high end for absorbance readings.

A sulfonic acid stop reagent of the invention, such as a compound of Formula I (i.e., R—$SO_3H$, wherein R is defined herein) is then added to the reaction composition. In exemplary modes of practice, the reagent is methanesulfonic acid or sulfamic acid, or combinations thereof. The stop reagent is soluble in the reaction composition and mixing can therefore be rapid. In an exemplary mode of practice, the stop reagent is 2× concentrated, or thereabouts, so the volume of stop reagent added to the well is approximately the same as the reaction volume in the well. For example, 100 μL of stop reagent is added to 100 μL of the reaction composition. Exemplary concentrations of stop reagent are in the range of about 1.5× to about 5×, which can be used to facilitate rapid mixing of the stop reagent and reaction components.

In some aspects the stop reagent is added to the reaction composition to provide a final concentration of stop reagent in the range of about 0.02 M to about 2.0 M, about 0.02 M to about 1 M, about 0.02 M to about 0.5 M, or about 0.02 to 0.2 M.

After the addition of the stop reagent, the reaction composition can optionally be described in terms of its pH. The acidic nature of the stop reagent generally results in a lowering of the pH of the reaction composition after it is added. In some cases the pH of the reaction composition is in the range of about 0.2 to about 4, or more specifically in the range of about 0.5 to about 2.

Optionally, depending on the particular stop reagent used, and also the type of chromogenic substrate, a cosolvent can be included in the stop reagent composition. As previously discussed, the cosolvent can ensure the reagents of the reaction composition be maintained in soluble form and do not precipitate out of solution upon addition of the stop reagent. Co-solvents such as alcohols, polyalcohols, dimethylsulfoxide, dimethylformamide, acetonitrile and similar solvents as previously described, can be used at a final concentration following addition of the stop reagent in the range of about 1% (v/v) to about 50% (v/v), or about 5% (v/v) to about 25% (v/v).

In methods using TMB as the chromogenic compound, the color of the reaction composition can transition to yellow corresponding to the two-electron oxidation product of TMB ($\lambda_{max}$ 450). The stop reagent of the invention can stabilize the two-electron oxidation product, resulting in a yellow composition that maintains high levels of absorbance at about 450 nm when monitored spectrophotometrically.

Analysis of the reaction mixture is performed under "stopped" conditions. By this it is meant that the reaction is allowed to proceed for a predetermined period and then terminated with a stop reagent of the invention. Without being bound by theory, it is thought that in the least, the addition of the stop reagent terminates the reaction by being a non-specific inhibitor of the enzyme, such as to sequester metal ions that are normally present for enzyme activity. However, the sulfonic acid stop reagent of the invention offers an advantage in that it stabilizes the chromogenic reaction product after the reaction has been stopped. For example, the stop reagents of the invention can stabilize the color of the chromogenic reaction product so that it minimizes change in absorbance characteristics of the chromogenic reaction product after it is added.

Figure 1:
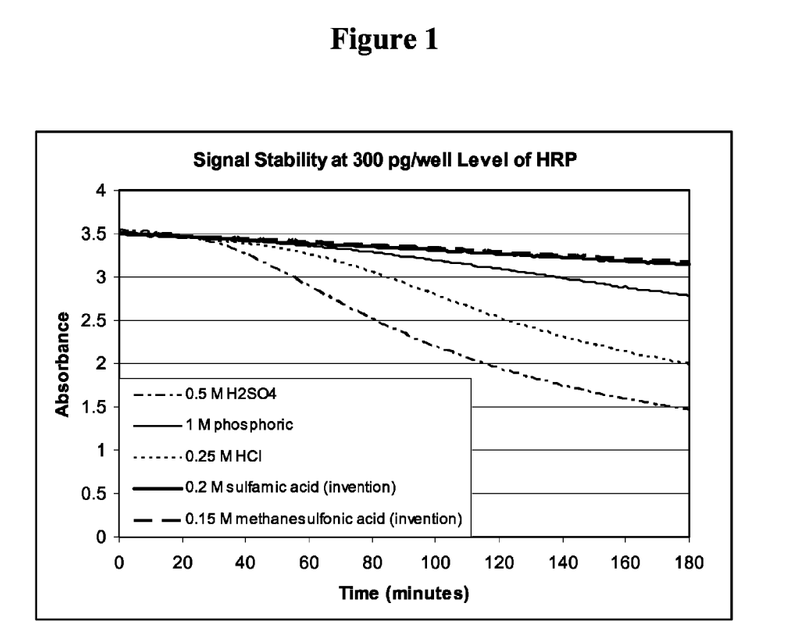
FIG. 1 is a graph showing the change in absorbance of tetramethylbenzidine (TMB) over time after the addition of various acidic stop reagents to a color-generating reaction mixture of TMB, horseradish peroxidase (300 pg/well), and hydrogen peroxide.

For example, with reference to FIG. 1, in the presence of stop reagents of the invention such as 0.2 M sulfamic acid or 0.15 M methanesulfonic acid, the stopped compositions exhibit nominal loss of absorbance at 450 nm, as compared to conventional stop reagents of 0.5 M $H_2SO_4$, 1 M phosphoric acid, or 0.25 M HCl, over extended periods of time. This can provide substantial improvements in the quality of analyte analysis, and lead to more accurate measurements of the amount of analyte in a sample. When analysis is performed using a multi-well format (such as a 96-well plate) the amount of time needed to add and mix the stop reagent into the wells may be significant, especially if analysis is performed using manual pipetting procedures. The loss of absorbance seen using conventional approaches (e.g., using 0.5 M $H_2SO_4$) can lead to sample-to-sample variations that may not accurately represent the actual amount of analyte in a sample. Use of the stop reagents of the invention significantly minimizes the loss of absorbance, resulting in more accurate measurements of analyte amounts. This also affords the user more time to carry out the assays, which can allow the throughput of the assays (i.e., the number of assays performed) within a single reaction batch to be increased.

Optionally, aspects of the invention can be described in the capacity of the stop reagent to stabilize the chromogenic product over a determined period of time with reference to absorption properties of the chromogenic product. For example, in some aspects the stop reagent stabilizes the chromogenic substrate so that it exhibits less than a 15% reduction, less than a 10% reduction, or less than a 5% reduction in absorbance at 60 minutes after addition of the stop reagent; less than a 20% reduction, less than a 15% reduction, or less than a 10% reduction in absorbance at 120 minutes after addition of the stop reagent; or less than a 30% reduction, less than a 25% reduction, or less than a 20% reduction in absorbance at 180 minutes after addition of the stop reagent In some methods of analyzing, such as using a direct or sandwich immunoassay as described herein, and the reagents employed, the absorbance of the chromogenic product as determined by a spectrophotometric method will be directly proportional to the amount of analyte in the sample. Where one is interested in a qualitative result or a semi-quantitative result, such as determining whether the amount of analyte is above a predetermined threshold, versus determining the concentration of analyte, the amount of peroxidase enzyme and/or chromogenic substrate can be selected to provide a clear signal as compared to the absence of analyte or analyte below the predetermined value.

For quantitation, absorbance can be accurately measured using appropriate hardware and software if desired. Controls can be employed, where the signal to concentration of the analyte is determined, so that the signal can be directly related to the concentration of analyte in the assayed sample. In this manner, both the presence and the amount of analyte in the sample can be determined. Simple spectrophotometers, such as UV/VIS spectrophotometers for wavelengths between 175 nm and 900 nm capable of determining the absorbance of a sample are commercially available, for example, from Perkin Elmer. In analyzing the sample, a light of a specific wavelength, such as selected by an optical filter or monochromator, is transmitted through the sample, and a detector measures the percentage of the initial transmitted through the sample. The amount of transmitted light is generally inversely proportional to the amount of analyte in the sample.

In other modes of practice, analysis is performed using a microplate reader. A variety of microplate readers capable of accommodating and analyzing the absorbance of samples in the wells of 96-well plates, are commercially available, from, for example BioTek (Winooski, Vt.).

Example 1

Methanesulfonic acid and sulfamic acid were compared to conventional stop reagent acids of sulfuric acid, hydrochloric acid and phosphoric acid to stop and stabilize a HRP TMB reaction.

To aliquots of 12 mL of TMB substrate (TMBW, SurModics, Inc.) were added either 35 µL or 5 µL of horseradish peroxidase (HRP) at 1 µg/mL. The solutions were mixed and the substrate plus HRP was distributed into a 96 well plate (100 µL/well). This resulted in TMB containing two HRP levels, 300 pg/well or 40 pg/well. One hundred microliters of TMBW was also added to a set of wells as no HRP blanks. After the blue color had developed so that the 300 pg/well conditions had an absorbance of approximately 1.5 at 650 nm (approximately 15 minutes), 100 µL of the stop reagents were added. The absorbance at 450 nm was them monitored for 3 hours with a reading every minute. There was an N of three for each HRP level/stop reagent combination and an N of 2 for the blanks.

Figure 2:
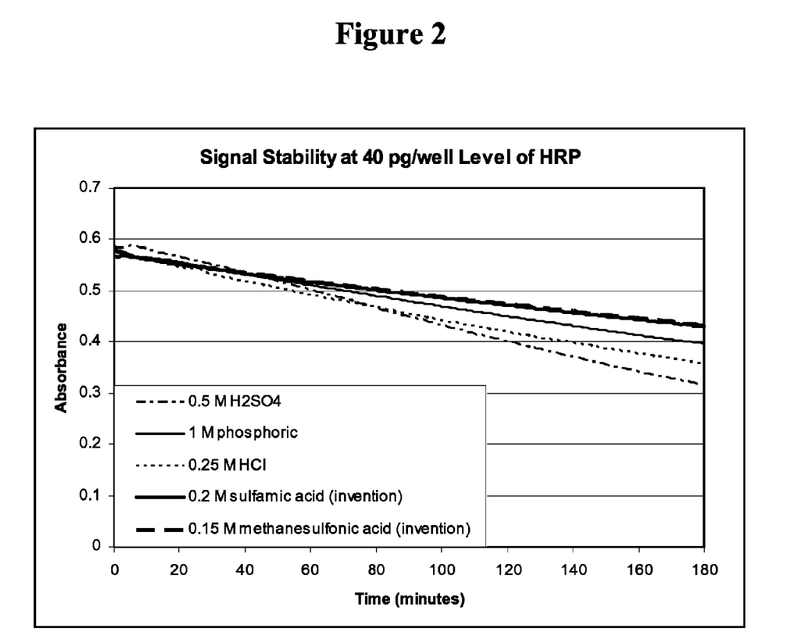
FIG. 2 is a graph showing the change in absorbance of tetramethylbenzidine (TMB) over time after the addition of various acidic stop reagents to a color-generating reaction mixture of TMB, horseradish peroxidase (40 pg/well), and hydrogen peroxide.

Table 2 and FIGS. 1 and 2 summarize the experimental results. The sulfonic acids had much more stabile signals for the entire 180 minutes. Table 1 provides ratios of the signal after three hours compared to the signal at 5 minutes after addition of the stop reagent. The methanesulfonic acid and sulfamic acid showed more stabile signals than the reference acids, and the differences were more pronounced at the higher HRP level.

TABLE 2

| Values are absorbance (A450) at 180 minutes divided by 5 minutes | High HRP (300 pg/well) | Low HRP (40 pg/well) | no HRP (Blank) |
| --- | --- | --- | --- |
| 0.5M H2SO4 (Reference) | 0.41 | 0.53 | 1.00 |
| 1M phosphoric (Reference) | 0.79 | 0.70 | 1.07 |
| 0.25M HCl (Reference) | 0.57 | 0.63 | 1.04 |
| 0.2M sulfamic acid (Invention) | 0.90 | 0.76 | 1.06 |
| 0.15M methanesulfonic acid (Invention) | 0.90 | 0.76 | 1.11 |

Example 2

A model assay that used biotinylated mouse IgG as the analyte was performed to investigate the stability of the resulting standard curves with the different stop reagents. Antibodies and streptavidin-HRP were obtained from Jackson Immunoresearch. Plates were coated with rabbit anti-mouse antibody (0.1 µg/well). Coated plates were incubated with a dilution series of biotinylated mouse IgG for 2 hours. The plates were then washed with PBS-Tween and then incubated for 20 minutes with strepavidin-HRP (1 µg/mL). After washing, 100 µL of TMB substrate was added to each well. The plate was allowed to develop until the highest absorbances were approximately 1.5 at 650 nm (approximately 15 minutes) and then 100 µL of the different stop reagents were added.

Figure 3:
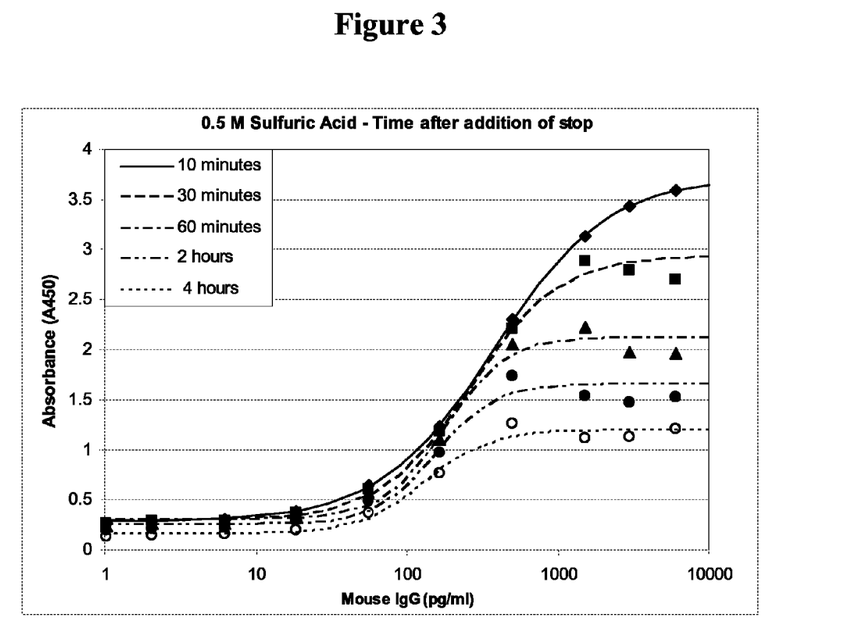
FIG. 3 is a graph showing the differences in absorbance of tetramethylbenzidine (TMB) at increasing amounts of analyte (as reflected by IgG concentration) measured at different times after the addition of 0.5 M sulfuric acid stop reagent to a color-generating reaction mixture of TMB, horseradish peroxidase, and hydrogen peroxide.
Figure 4:
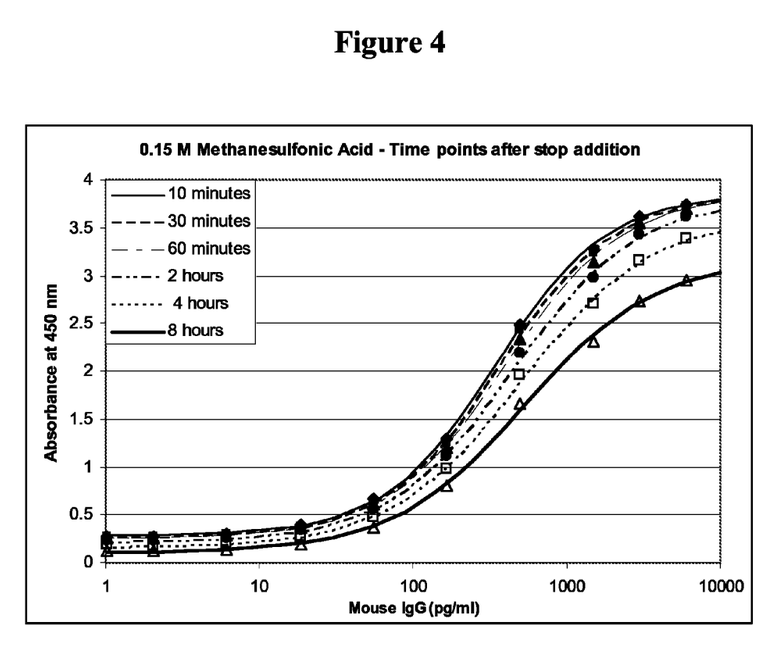
FIG. 4 is a graph showing the differences in absorbance of tetramethylbenzidine (TMB) at increasing amounts of analyte (as reflected by IgG concentration) measured at different times after the addition of 0.15 M methanesulfonic acid stop reagent to a color-generating reaction mixture of TMB, horseradish peroxidase, and hydrogen peroxide.
Figure 5:
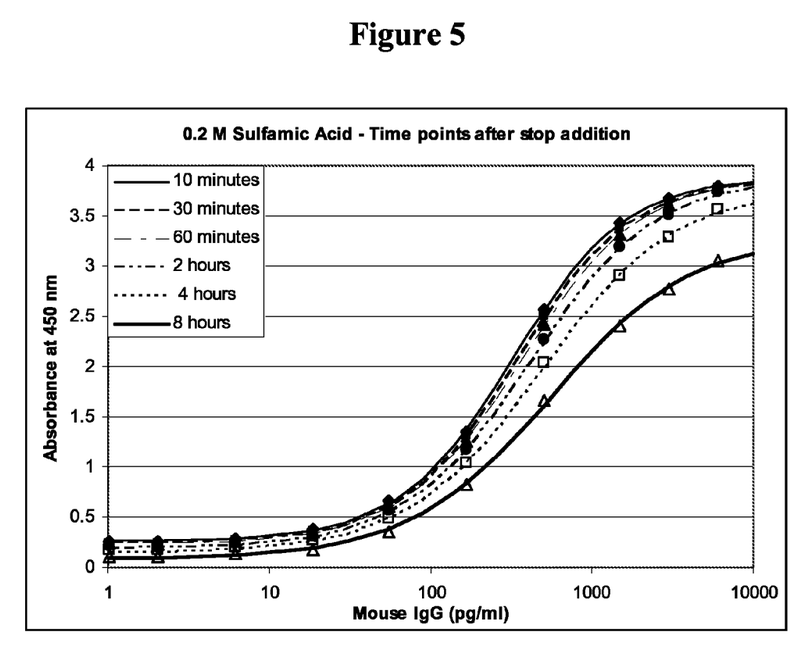
FIG. 5 is a graph showing the differences in absorbance of tetramethylbenzidine (TMB) at increasing amounts of analyte (as reflected by IgG concentration) measured at different times after the addition of 0.2 M sulfamic acid stop reagent to a color-generating reaction mixture of TMB, horseradish peroxidase, and hydrogen peroxide.

Three stop reagents were used: 0.15 M methanesulfonic acid, 0.2 M sulfamic acid and 0.5 M sulfuric acid. The absorbance at 450 nm was then monitored for eight hours, reading every 2.5 minutes. There was an N of four for each mouse IgG level/stop reagent combination. FIGS. 3-5 show the mouse IgG standard curves (4PL Fits) generated at selected time points. FIG. 3 is the result for the sulfuric acid comparison which shows that even after 30 minutes the ability to accurately quantitate across the across the dynamic range cannot be performed at higher analyte concentrations. FIGS. 4 and 5 demonstrate the results for methanesulfonic acid and sulfamic acid. The standard curves are very stabile for two hours and are also well fitted even eight hours after the addition of the stop reagent.

Example 3

A HRP assay was performed comparing other sulfonic acids to sulfuric acid in an HRP assay. Experiments were done using HRP alone as described in Example 1, except that the plates were read for only 90 minutes. Tables 2-4 report the results for the 300 pg/well condition where the stability difference is most pronounced.

As reflected in Table 3, para-toluenesulfonic acid (p-TSA) and 1-acrylamido-2 methylpropanesulfonic acid (AMPS) were used as stop reagents and compared to sulfuric acid. The p-TSA caused precipitation of reagent in the wells when it was dissolved in water alone. TMB was able to be maintained in solution by the addition of 20% DMSO to the stop reagent solution without adverse affects on the reaction or ability to analyze the reaction product. Tables 4 and 5 demonstrate that both ethanesulfonic acid and propanesulfonic acid also generate more stabile signals than the sulfuric acid reference conditions.

TABLE 3

| Stop Reagent | pH | A450 at 5 minutes | A450 at 90 minutes | 90 minute/5 minute ratio |
|---|---|---|---|---|
| 0.5N H2SO4 (reference) | | 3.398 | 2.548 | 0.750 |
| 0.2M p-toluenesulfonic acid | 0.93 | 3.441 | 2.652 | precipitated |
| 0.2M p-toluenesulfonic acid in 20% DMSO/water | 1.02 | 2.903 | 2.894 | 0.997 |
| 0.2M 1-acrylamido-2 methylpropanesulfonic acid (AMPS) | 1.04 | 3.306 | 3.105 | 0.939 |

TABLE 4

| Stop Reagent | pH | A450 at 5 minutes | A450 at 90 minutes | 90 minute/5 minute ratio |
|---|---|---|---|---|
| 0.5N H2SO4 (reference) | | 3.540 | 2.241 | 0.633 |
| 0.1M ethanesulfonic acid | 1.16 | 3.392 | 3.194 | 0.942 |
| 0.15M ethanesulfonic acid | 1.01 | 3.445 | 3.251 | 0.944 |
| 0.2M ethanesulfonic acid | 0.9 | 3.452 | 3.262 | 0.945 |
| 0.15M methanesulfonic acid | 0.99 | 3.486 | 3.292 | 0.945 |

TABLE 5

| Stop Reagent | pH | A450 at 5 minutes | A450 at 90 minutes | 90 minute/5 minute ratio |
|---|---|---|---|---|
| 0.5N H2SO4 (reference) | | 3.466 | 1.679 | 0.485 |
| 0.1M propanesulfonic acid | 1.16 | 3.355 | 3.149 | 0.939 |
| 0.15M propesulfonic acid | 1.01 | 3.411 | 3.215 | 0.943 |
| 0.2M propanesulfonic acid | 0.9 | 3.427 | 3.234 | 0.944 |
| 0.15M methanesulfonic acid | 0.99 | 3.408 | 3.226 | 0.947 |

What is claimed is:

1. A kit for colorimetric analysis comprising:
   a chromogenic substrate capable of forming a chromogenic reaction product, wherein the chromogenic substrate is a benzidine compound of formula:

wherein X, X', Y, Y', R, and R' are independently hydrogen, alkyl, alkoxy, wherein the alkyl or alkoxy group(s), if present, have four or less carbon atoms, and
   a composition comprising a sulfonic acid, wherein the sulfonic acid is a compound of formula $R-SO_3H$, wherein R is selected from the group consisting of methyl, ethyl, propyl, and $-NH_2$, and wherein the composition is configured for addition to a solution composition comprising the chromogenic reaction product, wherein the sulfonic acid provides the solution composition with a pH of 2.0 or less.

2. The kit of claim 1 wherein;
   the chromogenic substrate is tetramethylbenzidine (TMB); and
   the sulfonic acid is methanesulfonic acid or sulfamic acid.

3. The kit of claim 1 further comprising a peroxidase, an oxidase, or a conjugate of a peroxidase or an oxidase.

4. The kit of claim 3 further comprising an analyte specific binding member.

5. The kit of claim 3 further comprising an analyte positive control, an analyte negative control, or mixtures thereof.

6. The kit of claim 3 further comprising an analysis plate upon which a colorimetric analysis can be performed.

7. The kit of claim 3 wherein the peroxidase and/or oxidase is selected from the group consisting of horseradish peroxidase, soybean peroxidase, glucose oxidase, galactose oxidase, xanthine oxidase, lactoperoxidase, microperoxidase, NADH peroxidase, NADPH peroxidase, fatty-acid peroxidase, and catalase.

* * * * *